(12) United States Patent
Klug et al.

(10) Patent No.: US 8,389,756 B2
(45) Date of Patent: Mar. 5, 2013

(54) METHOD FOR PRODUCING ALKOXYLATED PHOSPHORIC ACID TRIESTERS

(75) Inventors: Peter Klug, Grossostheim (DE);
Franz-Xaver Scherl, Burgkirchen (DE);
Waltraud Simsch, Kelkheim (DE);
Adelgunde Oberhauser, Neuoetting (DE)

(73) Assignee: Clariant Finance (BVI) Limited, Tortola (VG)

( * ) Notice: Subject to any disclaimer, the term of this patent is extended or adjusted under 35 U.S.C. 154(b) by 172 days.

(21) Appl. No.: 12/671,809

(22) PCT Filed: Jul. 29, 2008

(86) PCT No.: PCT/EP2008/006222
§ 371 (c)(1),
(2), (4) Date: Jul. 29, 2010

(87) PCT Pub. No.: WO2009/015860
PCT Pub. Date: Feb. 5, 2009

(65) Prior Publication Data
US 2011/0040116 A1 Feb. 17, 2011

(30) Foreign Application Priority Data
Aug. 2, 2007 (DE) .......................... 10 2007 036 188

(51) Int. Cl.
*C07F 9/09* (2006.01)
(52) U.S. Cl. ........................................ 558/89
(58) Field of Classification Search ....................... 558/89
See application file for complete search history.

(56) References Cited

U.S. PATENT DOCUMENTS

| | | |
|---|---|---|
| 2,895,787 A | 7/1959 | Hall |
| 3,275,667 A | 9/1966 | Bohunek et al. |
| 4,180,532 A | 12/1979 | Chakrabarti et al. |
| 4,220,611 A | 9/1980 | Wolf |
| 5,192,462 A | 3/1993 | Gloor et al. |
| 6,120,780 A | 9/2000 | Dipuis et al. |
| 6,147,034 A | 11/2000 | Jones et al. |
| 6,264,965 B1 | 7/2001 | Roulier et al. |
| 6,448,297 B1 | 9/2002 | Turowski-Wanke et al. |
| 2003/0219398 A1 | 11/2003 | Loeffler et al. |
| 2003/0235598 A1 | 12/2003 | Klug et al. |
| 2004/0068050 A1 | 4/2004 | Miller et al. |
| 2004/0109835 A1 | 6/2004 | Loffler et al. |
| 2005/0112081 A1 | 5/2005 | Loeffler et al. |
| 2006/0069278 A1 | 3/2006 | Stehr et al. |
| 2006/0153792 A1 | 7/2006 | Arnaud et al. |
| 2007/0275854 A1 | 11/2007 | Hess et al. |
| 2010/0260696 A1 | 10/2010 | Klug et al. |
| 2010/0310483 A1 | 12/2010 | Klug et al. |
| 2011/0003010 A1 | 1/2011 | Klug et al. |
| 2011/0229427 A1 | 9/2011 | Klug et al. |
| 2011/0230449 A1 | 9/2011 | Klug et al. |

FOREIGN PATENT DOCUMENTS

| | | |
|---|---|---|
| DE | 35 42 441 | 6/1987 |
| DE | 100 16 875 | 10/2001 |
| DE | 10 2004 046 356 | 3/2006 |
| DE | 10 2004 047 092 | 3/2006 |
| EP | 0 510 246 | 10/1992 |
| EP | 0 816 403 | 1/1998 |
| EP | 1 005 857 | 6/2000 |
| EP | 1 344 517 | 9/2003 |
| EP | 1 344 518 | 9/2003 |
| EP | 1 352 644 | 10/2003 |
| EP | 1 407 813 | 4/2004 |
| EP | 1 514 537 | 3/2005 |
| EP | 1 518 900 | 3/2005 |
| GB | 2 023 606 | 1/1980 |
| JP | 09-020613 | 1/1997 |
| JP | 09-268193 | 10/1997 |
| JP | 2000-178288 | 6/2000 |
| SU | 1435579 | 11/1988 |
| WO | WO 92/17159 | 10/1992 |
| WO | WO 97/19748 | 6/1997 |
| WO | WO 97/42252 | 11/1997 |
| WO | WO 98/00094 | 1/1998 |
| WO | WO 02/43689 | 6/2002 |
| WO | WO 2004/030605 | 4/2004 |
| WO | WO 2005/090366 | 9/2005 |
| WO | WO 2009/015858 | 2/2009 |

OTHER PUBLICATIONS

International Search Report for PCT/EP2008/006218 dated Jan. 14, 2010.
Translation of International Preliminary Report on Patentability for PCT/EP2008/006218, Jan. 14, 2010.
International Search Report for PCT/EP2008/006219 dated Jul. 6, 2009.

(Continued)

*Primary Examiner* — Shawquia Young
(74) *Attorney, Agent, or Firm* — Tod A. Waldrop

(57) ABSTRACT

The invention relates to a method for producing phosphoric acid triesters of formula (I). According to said method, phosphoric acid or a phosphoric acid derivative selected from orthophosphoric acid, tetraphosphoric decaoxide and polyphosphoric acid is reacted with alkoxylated alcohols of formulae (II) $R_1$—$(OA_1)_x$-OH, (III) $R_2$—$(OA_2)_y$-OH, and (IV) $R_3$—$(OA_3)_z$-OH, in the molar ratio phosphoric acid or phosphoric acid derivative to alkoxylated alcohol of 1:2.5 to 1:3.3, at between 200 and 240° C.

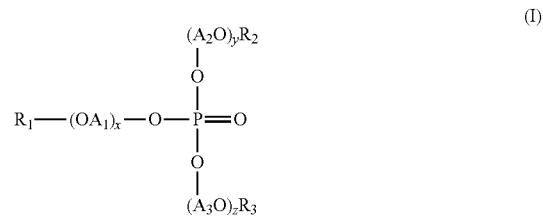

5 Claims, No Drawings

OTHER PUBLICATIONS

Translation of International Preliminary Report on Patentability for PCT/EP2008/006219, Jul. 6, 2009.
International Search Report for PCT/EP2008/006220, dated Jan. 15, 2009.
Translation of International Preliminary Report on Patentability for PCT/EP2008/006220, Jan. 15, 2009.
International Search Report for PCT/EP2008/006221 dated Jul. 9, 2009.
Translation of International Preliminary Report on Patentability for PCT/EP2008/006221, Jul. 9, 2009.
International Search Report for PCT/EP2008/006222 dated Jul. 6, 2009.
Translation of International Preliminary Report on Patentability for PCT/EP2008/006222, Jul. 6, 2009.
International Search Report for PCT/EP2009/000499 dated Dec. 21, 2009.
Translation of International Preliminary Report on Patentability for PCT/EP2009/000499, Dec. 21, 2009.
Database WPI Week 198921 Thomson Scientific, London, GB; AN 1989-157370 XP002533271 & SU 1 435 579 A (Macromolecular CPDS Inst) (Nov. 7, 1988).
Database Chemabs Chemical Abstracts Service, Columbus, Ohio, US; 1984, Polkovnichenko, I.T. et al,: "Solubilizing power of alkyl ethoxy phospates" XP002533694.
English Abstract of DE 35 42 441, Jun. 4, 1987.
English Abstract of DE 100 16 875, Oct. 18, 2001.
English Abstract of EP 0 816 403, Jan. 7, 1998.
English Abstract of JP 2000-178288, Jun. 27, 2000.
English Abstract of JP 09-020613, Jan. 21, 1997.
English Abstract of JP 09-268193, Oct. 14, 1997.
English Translation of SIPO Office Action for 200880101583.X, dated Dec. 7, 2011.

METHOD FOR PRODUCING ALKOXYLATED PHOSPHORIC ACID TRIESTERS

The invention relates to a process for preparing phosphoric triesters from phosphoric acid or chlorine-free phosphoric acid derivatives and alkoxylated fatty alcohols.

Phosphoric triesters are unobjectionable from the standpoints of toxicology and ecotoxicology, are skin-kind by virtue of their neutral pH levels, and are highly suitable for use as thickeners in cosmetic formulations.

Alkyl- and alkenylphosphoric esters are typically prepared by condensing fatty alcohols with diphosphorus pentoxide or orthophosphoric acid, giving mixtures of mono-/di-/triester, with a major fraction of monoester and diester.

JP 09-268193 describes a method of preparing phosphoric triesters by reacting phosphorus oxychloride with a fatty alcohol or an alkoxylated fatty alcohol in the presence of a catalyst selected from $TiCl_4$, $MgCl_2$ or $AlCl_3$. The disadvantage of this preparation process is that HCl is formed, which is removable only with great effort. Phosphoric triesters with chlorine-containing impurities, however, are unsuitable for use in cosmetic formulations.

The object was therefore to provide a process for preparing phosphoric triesters that allows access to chlorine-free phosphoric triesters, preferably with a triester fraction of more than 80% by weight.

It has been found, surprisingly, that this object is achieved by means of a process for preparing phosphoric triesters, distinguished by the reaction of phosphoric acid or chlorine-free phosphoric acid derivatives, more particularly with the exception of phosphorus oxychlorides, with alkoxylated fatty alcohols at temperatures in the range from 200 to 240° C.

The present invention accordingly provides a process for preparing phosphoric triesters of the formula (I)

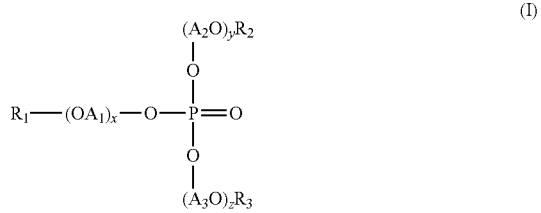

in which $R_1$, $R_2$ and $R_3$ may be alike or different and are a linear or branched, saturated alkyl group having 6 to 30, preferably 8 to 22, and more preferably 12 to 18 carbon atoms, a linear or branched, mono- or polyunsaturated alkenyl group having 6 to 30, preferably 8 to 22 and more preferably 12 to 18 carbon atoms, or an aryl group, more particularly a phenyl group, which may be substituted by 1 to 3 branched alkyl groups each independently of one another containing 3 to 18 and preferably 4 to 12 carbon atoms, the individual groups $(OA_1)_x$, $(A_2O)_y$ and $(A_3O)_z$ in each case independently of one another are composed of units selected from $CH_2CH_2O$, $C_3H_6O$ and $C_4H_8O$ it being possible for the units $CH_2CH_2O$, $C_3H_6O$ and $C_4H_8O$ within the individual groups $(OA_1)_x$, $(A_2O)_y$ and $(A_3O)_z$ to be in blockwise or randomly distributed arrangement, and x, y and z each independently of one another are a number from 10 to 150, preferably from 25 to 120, more preferably from 40 to 120, and with particular preference from 51 to 100, which comprises a) reacting phosphoric acid or a phosphoric acid derivative selected from orthophosphoric acid, tetraphosphorus decaoxide, and polyphosphoric acid with alkoxylated alcohols of the formula (II), (III) and (IV)

where $R_1$, $R_2$, $R_3$, $(OA_1)_x$, $(A_2O)_y$ and $(A_3O)_z$ possess the definitions stated in formula (I), b) in a molar ratio of phosphoric acid or phosphoric acid derivative to alkoxylated alcohol of 1:2.5 to 1:3.3, c) at 200 to 240° C., preferably at 220 to 230° C.

The alkoxylated alcohols of the formulae (II), (III) and (IV) may be alike or different.

It is preferred to use orthophosphoric acid as reactant.

With further preference use is made as alkoxylated alcohols of the formulae (II), (III) and (IV), which may be alike or different, of fatty alcohol ethoxylates, preferably fatty alcohol ethoxylates having 25 to 150 EO units ($EO=CH_2CH_2O$), more preferably having 40 to 120 EO units, and with particular preference having 51 to 100 EO units, the respective fatty alcohol residue $R_1O—$, $R_2O—$ and $R_3O—$ being derived from alcohols selected from octanol, decanol, dodecanol, tetradecanol, hexadecanol, octadecanol, eicosanol, behenyl alcohol, fatty alcohols with C-chain cuts between 8 and 22, preferably $C_{10}/C_{12}$ fatty alcohol, $C_{12}/C_{14}$ fatty alcohol, $C_{12}/C_{15}$ fatty alcohol, and $C_{16}/C_{18}$ fatty alcohol, branched fatty alcohols, preferably Guerbet alcohols, and monounsaturated fatty alcohols, preferably delta-9-cis-hexadecanol, delta-9-cis-octadecanol, trans-9-octadecanol and cis-delta-11-octadecanol.

With particular preference the alkoxylated alcohols of the formulae (II), (III) and (IV) are alike or different and are selected from $C_{16/18}$ fatty alcohol ethoxylates having 10 to 150 ethylene oxide units, preferably having 25 to 120 ethylene oxide units, more preferably $C_{16/18}$ fatty alcohol ethoxylate having 25 ethylene oxide units, $C_{16/18}$ fatty alcohol ethoxylate having 50 ethylene oxide units or $C_{16/18}$ fatty alcohol ethoxylate having 80 ethylene oxide units.

Further-preferred alkoxylated alcohols of the formulae (II), (III) and (IV), which may be alike or different, are fatty alcohol ethoxypropoxylates, preferably fatty alcohol ethoxypropoxylates having 25 to 149 $CH_2CH_2O$ units (EO) and 1 to 20 $C_3H_6O$ units (PO), more preferably having 40 to 120 EO and 2 to 10 PO units, and with particular preference having 51 to 100 DO and 2 to 5 PO units, the fatty alcohol residues being derived from the abovementioned fatty alcohols.

With further preference the process of the invention is performed such that the molar ratio of phosphoric acid or phosphoric acid derivative to alkoxylated alcohol is 1:3.

With further preference, the process of the invention is carried out without use of a solvent.

With further preference the process of the invention is carried out in the absence of a catalyst.

The phosphoric triesters of the formula (I) are pale in color and have iodine color numbers of <5, preferably <2.

Further provided by the present invention are phosphoric esters of the formula (I) obtainable by the process of the invention.

In one preferred embodiment of the invention the phosphoric esters of the formula (I) that are obtainable by the process of the invention are chlorine-free. This means in particular that these phosphoric esters of the formula (I) obtainable by the process of the invention contain no chlorine impurities.

The degree of conversion in the esterification is preferably >80.0%, i.e. more than 80.0% of all the esterifiable functions of the phosphoric acid or of the phosphoric acid derivatives are esterified. Particular preference is given to a degree of conversion >90.0%, with particular preference >95.0%.

Accordingly, the reaction products obtained by the process of the invention are, in particular, mixtures of phosphoric esters, the fraction of phosphoric triester being preferably more than 80.0% by weight and more preferably ≧85.0% by weight, based on the phosphoric ester mixture.

In one preferred embodiment of the invention, the phosphoric esters of the formula (I) that are obtainable by the process of the invention are present in a mixture of one or more phosphoric esters of the formula (V)

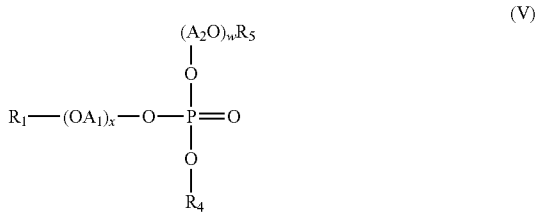

in which
$R_1$ is a linear or branched, saturated alkyl group having 6 to 30, preferably 8 to 22, and more preferably 12 to 18 carbon atoms, a linear or branched, mono- or polyunsaturated alkenyl group having 6 to 30, preferably 8 to 22 and more preferably 12 to 18 carbon atoms, or an aryl group, more particularly a phenyl group, which may be substituted by 1 to 3 branched alkyl groups, each independently of one another containing 3 to 18 and preferably 4 to 12 carbon atoms,
$R_4$ is H, $Li^+$, $Na^+$, $K^+$, $Mg^{++}$, $Ca^{++}$, $Al^{+++}$, $NH_4^+$ or quaternary ammonium ions $[HNR^a R^b R^c]^+$ in which $R^a$, $R^b$ and $R^c$ independently of one another are hydrogen, a linear or branched alkyl group having 1 to 22 carbon atoms, a linear or branched, mono- or polyunsaturated alkenyl group having 2 to 22 carbon atoms, a linear mono-hydroxy alkyl group having 2 to 10 carbon atoms, preferably a mono-hydroxyethyl or mono-hydroxypropyl group, or a linear or branched di-hydroxyalkyl group having 3 to 10 carbon atoms,
$R_5$ possesses the definition of $R_1$ or $R_4$,
the individual groups $(OA_1)_x$ and $(A_2O)_w$ in each case independently of one another are composed of units selected from $CH_2CH_2O$, $C_3H_6O$ and $C_4H_8O$ it being possible for the units $CH_2CH_2O$, $C_3H_6O$ and $C_4H_8O$ within the individual groups $(OA_1)_x$ and $(A_2O)_w$ to be in blockwise or randomly distributed arrangement,
x is a number from 10 to 150, preferably from 25 to 120, more preferably from 40 to 120 and with particular preference from 51 to 100,
w is 0 or a number from 10 to 150, preferably from 25 to 120, more preferably from 40 to 120 and with particular preference from 51 to 100, and
the amount of the phosphoric triesters of the formula (I) is greater than 80.0% by weight and preferably 85.0% by weight, based on the total weight of the phosphoric esters of formula (I) and formula (V), and the degree of neutralization of the unesterified phosphorus valences (P—OH) in the phosphoric esters of formula (V) can be between 0 and 100%.

The remaining free valences on the phosphorus atom may be acid groups, or else counterions, selected from $Li^+$, $Na^+$, $K^+$, $Mg^{++}$, $Ca^{++}$, $Al^{+++}$, $NH_4^+$, or quaternary ammonium ions $[HNR^a R^b R^c]^+$ in which $R^a$, $R^b$ and $R^c$ independently of one another are hydrogen, a linear or branched alkyl group having 1 to 22 carbon atoms, a linear or branched, mono- or polyunsaturated alkenyl group having 2 to 22 carbon atoms, a linear mono-hydroxy alkyl group having 2 to 10 carbon atoms, preferably a mono-hydroxyethyl or mono-hydroxypropyl group, and a linear or branched di-hydroxyalkyl group having 3 to 10 carbon atoms.

The degree of neutralization of the unsubstituted phosphorus valences (P—OH) may be between 0% and 100%.

In one preferred embodiment the phosphoric esters of the formula (V) are neutralized, with a degree of neutralization of 0-20.0%.

In another preferred embodiment of the invention the phosphoric esters of the formula (V) are neutralized, with a degree of neutralization of 20.1-100%.

According to the process of the invention it is possible, in addition to the phosphoric triesters of the formula (I) to obtain one or more phosphoric esters of the formula (V) in which $R^5$ possesses the definition of $R^4$, and w is 0. These compounds are mono-phosphoric esters, which are present preferably in amounts <3.0%, more preferably <1.0%, and with particular preference <0.1%, by weight, based on the total weight of the phosphoric esters of formula (I) and (V). In the mono-phosphoric esters it is possible for $R^4$ and $R^5$ to be alike or different.

According to the process of the invention it is possible, in addition to the phosphoric triesters of the formula (I) to obtain phosphoric esters of the formula (V) in which $R_5$ possesses the definition of $R_1$, and w is a number from 10 to 150, preferably from 25 to 120, more preferably from 40 to 120, and with particular preference from 51 to 100. These compounds are di-phosphoric esters, which are present preferably in amounts from 5.0% to 19.0%, more preferably from 10.0% to 17.0%, and with particular preference from 11.0% to 15.0%, by weight based on the total weight of the phosphoric esters of formula (I) and (V). In the di-phosphoric esters the radicals $R^1$ and $R^5$ may be alike or different.

The following examples and applications are intended to elucidate the invention in more detail, but without restricting it to them. All percentages are weight % (% by weight).

Preparation examples, general operational instructions:

In the preparation of the phosphoric esters of the invention, phosphoric acid (85% strength), and fatty alcohol ethoxylate are used in a defined molar ratio. For this purpose, all of the reactants are charged to a stirred apparatus with heating mantle, water separator with condenser, and vacuum connection. The mixture is heated to 100° C., evacuated three times to 100 mbar and then re-ventilated with nitrogen. After a further four hours of inertizing (introduction of nitrogen 20 liters/hour) at 100° C., the batch is heated, with introduction of nitrogen, to 230° C. and esterified (water discharge). The reaction times are 24 to 42 hours (reckoned for an esterification temperature of 230° C. upward), more particularly 40 hours. The residual acid number at this point is <3 mg KOH/g. This corresponds to a conversion of approximately 93% to 96% (based on initial acid number). After the end of the reaction, the product is cooled to 80° C., poured out into a tray, and the solidified melt is comminuted.

EXAMPLE 1

Ester formed from 17.3 g of phosphoric acid and 666.0 g of ceteareth-25 ($C_{16/18}$ fatty alcohol+25 mol of ethylene oxide) in a molar ratio of 1:3, residual acid number 1.7 mg KOH/g (95% conversion), $^{31}$P-NMR:diester/triester=11/89 mol %

EXAMPLE 2

Ester formed from 12.7 g of phosphoric acid and 701.3 g of ceteareth-50 ($C_{16/18}$ fatty alcohol+50 mol of ethylene oxide)

in a molar ratio of 1:3, residual acid number 0.8 mg KOH/g (97% conversion), $^{31}$P-NMR:diester/triester=13/87 mol %

EXAMPLE 3

Ester formed from 11.4 g of phosphoric acid and 935.1 g of ceteareth-80 ($C_{16/18}$ fatty alcohol+80 mol of ethylene oxide) in a molar ratio of 1:3, residual acid number 0.8 mg KOH/g (96% conversion), $^{31}$P-NMR:diester/triester=15/85 mol %

What is claimed is:

1. A process for preparing phosphoric acid triesters of the formula (I)

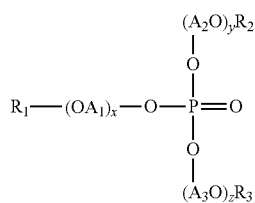

wherein $R_1$, $R_2$ and $R_3$ may be alike or different and are a linear or branched, saturated alkyl group having 6 to 30 carbon atoms, a linear or branched, mono- or polyunsaturated alkenyl group having 6 to 30 carbon atoms, or an aryl group, which may be substituted by 1 to 3 branched alkyl groups each independently of one another containing 3 to 18 carbon atoms, the individual groups $(OA_1)_x$, $(A_2O)_y$ and $(A_3O)_z$ in each case independently of one another are composed of units selected from the group consisting of $CH_2CH_2O$, $C_3H_6O$ and $C_4H_8O$ it being possible for the units $CH_2CH_2O$, $C_3H_6O$ and $C_4H_8O$ within the individual groups $(OA_1)_x$, $(A_2O)_y$ and $(A_3O)_z$ to be in blockwise or randomly distributed arrangement, and x, y and z each independently of one another are a number from 10 to 150, which comprises a) reacting phosphoric acid or a phosphoric acid derivative selected from the group consisting of orthophosphoric acid, tetraphosphorus decaoxide, and polyphosphoric acid with alkoxylated alcohols of the formula (II), (III) and (IV)

$R_1$—$(OA_1)_x$-OH    formula (II)

$R_2$—$(OA_2)_y$-OH    formula (III)

$R_3$—$(OA_3)_z$-OH    formula (IV)

where $R_1$, $R_2$, $R_3$, $(OA_1)_x$, $(A_2O)_y$ and $(A_3O)_z$ are defined as in formula (I), b) in a molar ratio of phosphoric acid or phosphoric acid derivative to alkoxylated alcohol of 1:2.5 to 1:3.3, c) at 200 to 240° C.

2. A process as claimed in claim 1, wherein orthophosphoric acid is used as reactant.

3. A process as claimed in claim 1, wherein the alkoxylated alcohols of the formulae (II), (III) and (IV) are alike or different and are selected from $C_{16/18}$-fatty alcohol ethoxylates having 10 to 150 ethylene oxide units.

4. A process as claimed in claim 1, which is carried out without use of a solvent.

5. A process as claimed in claim 1, which is carried out in the absence of a catalyst.

* * * * *